United States Patent
Wu et al.

(10) Patent No.: US 11,499,134 B2
(45) Date of Patent: Nov. 15, 2022

(54) METHOD FOR CULTURING GINSENG CELL WITH HIGH CONTENT OF GINSENOSIDE

(71) Applicant: Shenzhen XianSheng Science and Technology Development Co., Ltd., Guangdong (CN)

(72) Inventors: Dong Wu, Shenzhen (CN); Huaide Chen, Shenzhen (CN); Lili Cheng, Shenzhen (CN); Minxian Liu, Shenzhen (CN); Lili Hou, Shenzhen (CN); Yujia Liu, Shenzhen (CN); Yuanjian Ling, Shenzhen (CN)

(73) Assignee: Shenzhen XianSheng Science and Technology Development Co., Ltd., Shenzhen (CN)

( * ) Notice: Subject to any disclaimer, the term of this patent is extended or adjusted under 35 U.S.C. 154(b) by 0 days.

(21) Appl. No.: 17/160,482

(22) Filed: Jan. 28, 2021

(65) Prior Publication Data

US 2021/0147793 A1    May 20, 2021

Related U.S. Application Data

(63) Continuation-in-part of application No. 16/296,254, filed on Mar. 8, 2019, now abandoned.

(30) Foreign Application Priority Data

Jan. 24, 2019   (CN) .................... 201910066835.X

(51) Int. Cl.
| | |
|---|---|
| C12N 5/00 | (2006.01) |
| A61K 36/258 | (2006.01) |
| A01H 4/00 | (2006.01) |
| A23L 33/105 | (2016.01) |
| C12N 5/04 | (2006.01) |

(52) U.S. Cl.
CPC .......... *C12N 5/0025* (2013.01); *A01H 4/001* (2013.01); *A01H 4/005* (2013.01); *A23L 33/105* (2016.08); *A61K 36/258* (2013.01); *A61K 2236/00* (2013.01); *A61K 2236/51* (2013.01); *A61K 2800/82* (2013.01); *A61K 2800/84* (2013.01); *C12N 5/04* (2013.01); *C12N 2501/00* (2013.01); *C12N 2501/30* (2013.01)

(58) Field of Classification Search
CPC .......... C12N 5/00; C12N 5/0025; C12N 5/04; C12N 2500/00; C12N 2500/05; C12N 2500/34; C12N 2500/76; C12N 2501/00; C12N 2511/00; C12N 2521/00; A61K 36/258; A61K 2800/82; A61K 2800/84; A61K 2236/51; A61K 2236/00; A01H 4/005; A01H 4/001; A23L 33/105
See application file for complete search history.

(56) References Cited

PUBLICATIONS

Gantait et al, Biotechnological Interventions for Ginsenosides Production, Biomolecules, 2020, 10, 538; doi:10.3390/biom10040538, www.mdpi.com/journal/bimolecules pp. 1-18.*
Wilson and Roberts, Recent Advances Towards Development and Commercialization of Plant Cell Culture Processes for Synthesis of Biomolecules, Plant Biotechnology Journal, 2012, 10(3): 249-268, doi:10.1111/j.1467-7652.2011.00664.x. pp. 1-39 downloaded.*
Zhang et al, Effect of Three Different Drying Methods on Extraction and Separation of Ginsenosides from Fresh Ginseng, J. Chine Integr Med. Jul. 2004, vol. 2, No. 4, pp. 292-294.*
Zheng et al, Study on Transformnation of Ginsenosides in Different Methods, Hindawi, BioMed Research International, vol. 2017, article ID 8601027, pp. 1-10, https://doi.org/10.1155/2017/8601027.*
Zhang et al (JGR), Ginsenoside Production and Morphological Characterization of Wild Ginseng (*Panax ginseng* Meyer) Mutant Lines Induced by Y-irradiation (60Co) of Adventitious Roots, J. Ginseng Res. vol. 35, No. 3, pp. 283-293, 2011, http://dx.doi.org/10.5142/jgr.2011.35.3.283, http://ginsengres.org, pISSN: 1226-845.*
Wu and Lin, Elicitor-like effects of low-energy ultrasound on plant (*Panax ginseng*) cells: Induction of plant defense responses and secondary metabolite production, Applied Microbiology and Biotecvhnology 59, 21-57, 2002.*

(Continued)

*Primary Examiner* — Anne Marie Grunberg

(57) ABSTRACT

A method for culturing ginseng cell with high content of ginsenoside, including inducing ginseng cell line: after disinfected and sliced, ultrasonically treating old mountain ginseng, and culturing the old mountain ginseng in a culture medium; screening the ginseng cell line: choosing a variety of culture mediums and using hormones for cell separation and culture, selecting cell lines with better growth morphology and faster growth, and performing solid subculture and liquid suspension culture; optimizing conversion conditions: using acids to treat the chosen cell lines, and controlling the treatment temperature and treatment time, detecting ginsenosides Rg3 and Rh2 in the dried products, determining an optimal treatment condition according to the highest total amount; large-scale industrial production: according to the optimal treatment condition, performing the liquid suspension culture of the selected cell lines and scaling up the scale of culture to obtain large-scale industrial production of ginseng cell products.

5 Claims, 1 Drawing Sheet

(56) References Cited

PUBLICATIONS

Thanh et al, Optimization of ginseng cell culture in airlift bioreactors and developing the large-scale production system, Industrial Crops and Products 60 (2014) 343-348.*

Echendu et al, In vitro propagation of North American ginseng (*Panax quinquefolius* L.), In Vitro Cell Dev Diol—Plant (2011) 47:710-718, DOI 10.1007/s11627-011-9379-y.*

Millipore Sigma Explant Sterilization—Plant Tissue Culture Protocol, Commonly Used Disinfectants for Plant Tissue Culture, https://www.sigmaaldrich.com/US/en/technical-documents/protocol/cell-culture-and-cell-culture-analysis/plant-tissue-culture/explant-sterilization, downloaded Dec. 4, 2021.*

Yingchun Zhang, Regulation Activity of Plant Stem Cell and Telomere Length by Ginsenosides, Chinese Doctoral Dissertation Full-text Database Medical Science and Technology Series, E057-55, Nov. 30, 2015.

* cited by examiner

```
                                                        S1
┌──────────────────────────────────────────────────────────┐
│ inducing ginseng cell line: after disinfected and sliced, ultrasonically treating │
│ old mountain ginseng, and culturing the old mountain ginseng in a culture │
│                 medium to induce cell growth             │
└──────────────────────────────────────────────────────────┘
                              │
                              ▼                         S2
┌──────────────────────────────────────────────────────────┐
│ screening the ginseng cell line: choosing a variety of culture mediums and using │
│ different types of hormones with different concentrations for cell separation and │
│  culture, selecting one or several cell lines with better growth morphology and │
│   faster growth, and performing solid subculture and liquid suspension culture │
│                            respectively                  │
└──────────────────────────────────────────────────────────┘
                              │
                              ▼                         S3
┌──────────────────────────────────────────────────────────┐
│ optimizing conversion conditions: using a variety of weak acids with different │
│  concentrations to treat the chosen cell lines, and controlling the transformation │
│  temperature and transformation time, detecting ginsenosides Rg3 and Rh2 in │
│  the dried products, determining an optimal transformation condition according │
│           to the highest total amount of ginsenoside Rg3 and Rh2 │
└──────────────────────────────────────────────────────────┘
                              │
                              ▼                         S4
┌──────────────────────────────────────────────────────────┐
│    large-scale industrial production: according to the optimal transformation │
│ condition, performing the liquid suspension culture of the selected cell lines and │
│   scaling up the scale of culture to obtain large-scale industrial production of │
│   ginseng cell products with high yield and high content of ginsenoside after │
│                            transformation               │
└──────────────────────────────────────────────────────────┘
```

METHOD FOR CULTURING GINSENG CELL WITH HIGH CONTENT OF GINSENOSIDE

CROSS-REFERENCE TO RELATED APPLICATIONS

This application is a continuation-in-part application of U.S. patent application Ser. No. 16/296,254 filed on Mar. 8, 2019, which claims the benefit of Chinese Patent Application No. 201910066835.X filed on Jan. 24, 2019, all of which are incorporated herein by reference in their entireties.

TECHNICAL FIELD

The application relates to the field of medicinal plant biotechnology, in particular to a method for culturing ginseng cell with high content of ginsenoside through the induction, screening and transformation of ginseng cell lines.

BACKGROUND

Ginseng is a kind of perennial herb of Acanthopanax senticosus. It likes to be shady and cool. It mostly grows in the coniferous broad-leaved mixed forest or mixed forest on the gentle slope of the shady mountain. Because the root of ginseng is hypertrophy, it has a cylindrical or spindle-shaped structure and often has branches. The whole appearance is similar to human type, so it is called ginseng. According to traditional medicine, ginseng has the functions of tonifying vital energy, restoring pulse, strengthening lung and spleen, generating body fluid, relieving thirst, calming mind and improving intelligence, so it is used as the main medic of many kinds of prescriptions.

The traditional source of ginseng is mainly obtained through planting. Due to the limitation of land, climate and season, and the low content of ginsenoside, the quality and yield of ginseng cannot meet the market demand. At present, there are some technical methods to improve the production of ginsenoside through the research of ginseng cells, but there are some problems in this method, such as the instability of ginseng cells and the inability of stable passage, which makes it difficult for ginseng cells to form a stable industrial and large-scale production.

SUMMARY

Based on this, it is necessary to provide a method for culturing ginseng cell with high content of ginsenoside through induction, screening and transformation of ginseng cell lines in order to solve the technical problem that ginseng cells are unstable and difficult to stabilize mass production.

A method for culturing ginseng cell with high content of ginsenoside, comprising the following steps:

S1. inducing ginseng cell line: after disinfected and sliced, ultrasonically treating old mountain ginseng, and culturing the old mountain ginseng in a culture medium to induce cell growth;

S2. screening the ginseng cell line: choosing a variety of culture mediums and using different types of hormones with different concentrations for cell separation and culture, selecting one or several cell lines with better growth morphology and faster growth, and performing solid subculture and liquid suspension culture respectively;

S3. optimizing conversion conditions: using a variety of weak acids with different concentrations to treat the chosen cell lines, and controlling the transformation temperature and transformation time, detecting ginsenosides Rg3 and Rh2 in the dried products, determining an optimal transformation condition according to the highest total amount of ginsenoside Rg3 and Rh2;

S4. large-scale industrial production: according to the optimal transformation condition, performing the liquid suspension culture of time selected cell lines and scaling up the scale of culture to obtain large-scale industrial production of ginseng cell products with high yield and high content of ginsenoside after transformation.

In one embodiment, in step S1, a disinfection method is to remove epidermis of the old mountain ginseng washed by running water, soak it in alcohol for 30 s-1 min, and then disinfect it twice with 0.5-10% NaClO.

In one embodiment, disinfecting with NaClO includes 8 minutes of disinfection with 2% NaClO, 4 minutes of disinfection with 2% NaClO after washing with sterile water.

In one embodiment, the old mountain ginseng is sliced in CS cutting fluid and treated with ultrasonic wave in BIM solution, the CS cutting fluid includes PVP0.5% w/v, ascorbic acid 100 mg/L and citric acid 150 mg/L, the BIM solution includes WPM salt ¼ Content, sucrose 1% w/v, PVP0.5% w/v, ascorbic acid 100 mg/L and citric acid 150 mg/L.

In one embodiment, in step S1, the frequency of ultrasonic treatment is 5 KHz to 100 kHz, and the treatment time is 0.1 min to 10 min.

In one embodiment, the culture medium in step S2 includes MS culture medium, B5 culture medium or white culture medium, and the hormone includes one or more of 0.5 mg/l-6 mg/l of 2,4-D, NAA, IBA or KT.

In one embodiment, in step S3, citric acid, glacial acetic acid and ascorbic acid with the concentration of 0.1%-30% are used to treat the chosen cell lines. the transformation temperature is 60° C.-90° C., and the transformation time is 12 h-20 h.

In one embodiment, after drying, the product is extracted with 80% methanol, and the contents of Ginsenoside Rg3 and Rh2 are detected by HPLC.

In one embodiment, in step S4, when a laboratory shaker is selected, the scale of liquid suspension culture includes 250 ml, 500 ml, and 1 L; when an industrial fermenter is selected, the scale of liquid suspension culture includes 50 L, 100 L, and 500 L.

In one embodiment, when the industrial fermenter is selected, the aeration rate of fermenter 2-20 L/min, the tank pressure is 0.03-0.05 mpa, the inoculation amount is 20%-50%, and the culture time is 20-30 d.

The implementation of the method for culturing ginseng cell with high content of ginsenoside can promote the rapid growth and stable passage of ginseng cells, and improve the yield of ginseng cells; through the ultrasonic treatment of the sliced old mountain ginseng, the specific tissue in the sliced old mountain ginseng is inactivated, so as to realize the induced growth of ginseng cell line, and improve the content of ginsenoside Rg3 and Rh2 in ginseng cells. In this way, the waste of land resources caused by planting is avoided, and the cost is low. It can carry out industrial production, not limited by seasonal climate and other conditions, without pesticide residues and heavy metal pollution, and can be stably and continuously produced to meet the market demand.

DESCRIPTION OF THE DRAWINGS

The sole is a flow chart of a method for culturing ginseng cell with high content of ginsenoside in an embodiment of the application.

DETAILED DESCRIPTION OF THE PREFERRED EMBODIMENT

In order to make the above objects, features and advantages of the application more obvious and easier to understand, the specific implementation mode of the application is described in detail in combination with the drawings. Many specific details are set forth in the following description to facilitate a full understanding of the present application. However, the application can be implemented in many ways different from those described here. Those skilled in the art can make similar improvements without violating the connotation of the application. Therefore, the application is not limited by the specific embodiments disclosed below.

Referring to the sole figure, the application provides a method for culturing ginseng cell with high content of ginsenoside through the induction, screening and transformation of ginseng cell lines, the culture method comprises the following steps:

S1. inducing ginseng cell line: after disinfected and sliced, ultrasonically treating old mountain ginseng, and culturing the old mountain ginseng in a culture medium to induce cell growth;

Specifically, select the old mountain ginseng over 50 years old, wash the soil on the surface of the old mountain ginseng under running water, and then use a scalpel to cut off the epidermis and roots of the cleaned old mountain ginseng, so as to realize the pretreatment of the old mountain ginseng. Place the pretreated old mountain ginseng in an ultra-clean workbench, and use alcohol to soak and disinfect the old mountain ginseng for 30 s-1 min. Preferably, use 75% alcohol to soak and disinfect the old mountain ginseng for 1 minute. After alcohol disinfection, the epidermis of the old ginseng was rinsed with sterile water to remove the residual alcohol on the epidermis, and then the old ginseng was disinfected twice with 0.5-10% NaClO. Furthermore, disinfecting with NaClO includes 8 minutes of disinfection with 2% NaClO, 4 minutes of disinfection with 2% NaClO after washing with sterile water so as to kill the bacteria on the surface of old mountain ginseng and avoid the bacteria interfering with the cultivation of ginseng cells.

After the disinfection of old mountain ginseng, use sterile water to rinse the surface again to remove the NaClO solution from the epidermis of old mountain ginseng to prevent the NaClO solution from contacting the middle of the ginseng slice and corroding or even destroying the structure of ginseng cells during the slicing process to improve the reliability of ginseng cell culture operations. After rinsing with sterile water, the old mountain ginseng is sliced in CS cutting fluid containing PVP 0.5% w/v, ascorbic acid 100 mg/L and citric acid 150 mg/L to cut into slices with a thickness of 0.1-0.2 cm. The ginseng slices are then placed in the BIM solution shown in Table 1, also known as the browning inhibition medium for ultrasonic treatment. The frequency of ultrasonic treatment is 5 KHz to 100 kHz, and the treatment time is 0.1 min to 10 min.

TABLE 1

| Browning inhibition culture medium | |
|---|---|
| composition | content |
| WPM culture medium | ¼ salt |
| sucrose | 1% (w/v) |
| PVP Polyvinylpyrrolidone | 0.5% (w/v) |
| ascorbic acid | 100 mg/L |
| citric acid | 150 mg/L |
| | pH 5.8 |

It should be noted that the slicing of old mountain ginseng in CS cutting fluid and ultrasonic treatment in the environment of BIM solution are to prevent browning of old mountain ginseng, that is, to prevent oxidation of old mountain ginseng, so as to ensure the reliability of culture results. Preferably, the ginseng slices are treated with ultrasound at a frequency of 20 kHz in BIM solution for 5 min to make certain tissues in the slices, such as phloem, xylem and pith of old mountain ginseng, necrotic or inactivated, that is to say, only the cambium containing ginsenoside Rg3 and Rh2, that is, the meristem survived, so as to improve the content of ginsenoside Rg3 and Rh2 in the final product.

After ultrasonic treatment of the ginseng slices, sterile paper is used to absorb water on the surface of the ginseng slices, and the ginseng slices are placed in a culture medium for culture to induce the growth of ginseng cells.

S2. screening the ginseng cell line: choosing a variety of culture mediums and using different types of hormones with different concentrations for cell separation and culture, selecting one or several cell lines with better growth morphology and faster growth, and performing solid subculture and liquid suspension culture respectively;

Specifically, choose MS culture medium, B5 culture medium or white culture medium, and add one or more of 0.5 mg/l-6 mg/l of 2,4-D, NAA, IBA or KT to the corresponding culture medium for cell culture. It should be noted that in this embodiment, different concentrations and types of hormones can be selected for different kinds of culture medium to treat the ginseng tablets, so as to compare and obtain the test conditions with the best culture effect. In order to select one or several cell lines with better growth morphology and faster growth, B5 culture medium is used for cell culture of shenpian, and 3.0 mg/l IBA and 0.5 mg/l KT are added. Then the selected cell lines are subcultured in solid and liquid suspension respectively. The solid subculture and liquid suspension culture of cell lines need to be carried out in MS medium, and 3.0 mg/l 2, -4D and 6.0 mg/l NAA are added until the best cell line with fast growth rate and stable growth is selected.

S3. optimizing conversion conditions: using a variety of weak acids with different concentrations to treat the chosen cell lines, and controlling the transformation temperature and transformation time, detecting ginsenosides Rg3 and Rh2 in the dried products, determining an optimal transformation condition according to the highest total amount of ginsenoside Rg3 and Rh2;

Specifically, excellent cell lines are selected and cultured in liquid suspension for 21 days. After filtration through 300 mesh sieve, water equal to the fresh weight of cells is added, and citric acid, glacial acetic acid and ascorbic acid of different concentrations are added to treat the selected cell lines. The results showed that the concentration of citric acid, glacial acetic acid and ascorbic acid ranged from 0.1% to 30%, the transformation temperature is 60° C.-90° C., and the transformation time is 12 h-20 h. In the actual cultivation process, the transformation temperature could be 60° C., 75° C. and 90° C., and the transformation time could be 12 h, 14 h, 16 h and 20 h. A variety of ginseng cells treated with different conditions are obtained. The transformed product is collected and dried. The product is extracted with 80% methanol. The content of ginsenoside Rg3 and Rh2 is detected by HPLC. The conversion rate of rare ginsenoside in the product is evaluated according to the content of Ginsenoside Rg3 and Rh2. Preferably, citric acid with a concentration of 0.7% is added to the filtered cell line, and the transformation is continued for 16 hours at a transformation temperature of 90° C., and then the transformed product is collected. After drying, 0.1 g product is mixed with 10 ml methanol with a concentration of 80%. After ultrasonic extraction, filter it with a 0.22 um sieve, and use HPLC to detect the concentration of rare ginsenoside Rg3 and Rh2. The sum of the two can reach 12.8% of the converted product.

S4. large-scale industrial production: according to the optimal transformation condition, performing the liquid suspension culture of the selected cell lines and scaling up the scale of culture to obtain large-scale industrial production of ginseng cell products with high yield and high content of ginsenoside after transformation.

Specially, when a laboratory shaker is selected, the scale of liquid suspension culture includes 250 ml, 500 ml, and 1 L; when an industrial fermenter is selected, the scale of liquid suspension culture includes 50 L, 100 L, and 500 L. Furthermore, in the selection of industrial fermentor, it is necessary to optimize the fermentation conditions, such as aeration rate, tank pressure, inoculation amount and culture time. In this embodiment, the fermentor adopts the new microporous Bubbling Technology for fermentation, the aeration rate of the fermentor is 2-20 L/min, the tank pressure is 0.03-0.05 mpa, the inoculation amount is 20%-50%, and the culture time is 20-30 d. It is optimized that the aeration rate of fermenter is set to 3 L/min when 50 L or 100 L fermenter is used for liquid suspension culture, and the aeration rate of fermenter is set to 10 L/min when 5500 L fermenter is used for liquid suspension culture. The liquid suspension obtained under this condition is filtered through 300 mesh sieve, and the fresh weight of harvested cells reaches 120 g/L. Finally, large-scale industrial production of ginseng cell products with high yield and high content of rare ginsenosides after transformation is obtained.

The implementation of the method for culturing ginseng cell with high content of ginsenoside can promote the rapid growth and stable passage of ginseng cells, and improve the yield of ginseng cells; through the ultrasonic treatment of the sliced old mountain ginseng, the specific tissue in the sliced old mountain ginseng is inactivated, so as to realize the induced growth of ginseng cell line, and improve the content of ginsenoside Rg3 and Rh2 in ginseng cells. In this way, the waste of land resources caused by planting is avoided, and the cost is low. It can carry out industrial production, not limited by seasonal climate and other conditions, without pesticide residues and heavy metal pollution, and can be stably and continuously produced to meet the market demand.

The technical features of the above-mentioned embodiments can be arbitrarily combined. In order to make the description concise, all possible combinations of the technical features in the above-mentioned embodiments are not described. However, as long as there is no contradiction in the combination of these technical features, it should be considered as the scope of the description.

The above-mentioned examples only express several embodiments of the application, and the description is more specific and detailed, but it cannot be understood as a limitation on the scope of the application patent. It should be pointed out that for ordinary technicians in the art, a number of modifications and improvements can be made without departing from the concept of the application, which belong to the protection scope of the application. Therefore, the scope of protection of the application patent shall be subject to the attached claims.

What claimed is:

1. 1. A method for culturing ginseng cells having a high content of ginsenoside comprising:
   a. disinfecting a wild ginseng that is over 50 years old by washing the ginseng with running water, soaking the ginseng in alcohol for 30 s-1 min, and disinfecting the ginseng twice with 0.5-10% NaClO;
   b. slicing the ginseng in cutting fluid comprising 0.5% w/v Polyvinyl pyrrolidone (PVP), 100 mg/L ascorbic acid, and 150 mg/L citric acid;
   c. treating the ginseng with ultrasonic waves in browning inhibition culture medium comprising 25% Woody Plant medium (WPM), 1% w/v sucrose, 0.5% w/v PVP, 100 mg/L ascorbic acid, and 150 mg/L citric acid;
   d. culturing the ginseng in B5 culture medium supplemented with 3.0 mg/L 3-Indolebutyric acid (IBA) and 0.5 mg/L Kinetin (KT) to get multiple cell lines;
   e. selecting one or several cell lines showing fast growth and good growth morphology;
   f. culturing the selected cell lines on solid Murashige and Skoog (MS) medium supplemented with 3.0 mg/L 2,4-D and 6.0 mg/L Naphthalene acetic acid (NAA) followed by liquid suspension culture in Murashige and Skoog (MS) medium supplemented with 3.0 mg/L 2,4-D and 6.0 mg/L Naphthalene acetic acid (NAA);
   g. treating the cultured selected cell lines with different amounts and types of weak acids, temperatures, and times wherein the weak acids are selected from the group comprising citric acid, glacial acetic acid and ascorbic acid, the concentration of the weak acid is 0.1%-30%, the treatment temperature is 60° C.-90° C., and the treatment time is 12 h-20 h;
   h. collecting and drying the treated cell line cultures, extracting ginsenosides Rg3 and Rh2 with 80% methanol, selecting the treatment conditions resulting in the highest total amounts of ginsenoside Rg3 and Rh2 as indicated by HPLC to determine the optimal treatment conditions of the cultured selected cell lines;
   i. scaling up liquid suspension culture of the selected cell lines to realize large-scale industrial production of ginseng cell products having high amount of ginsenoside wherein the liquid suspension culture is produced in a laboratory shaker having a volume of 250 mL, 500 mL, or 1 L or wherein the liquid suspension culture is produced in an industrial fermenter having a volume of 50 L, 100 L, or 500 L; and
   j. extracting the ginsenosides produced from the cell cultures in accordance with the determined optimal treatment conditions.

2. The method of claim 1, wherein the ginseng is disinfected in 2% NaClO for 8 minutes, washed in sterile water, and further disinfected in 2% NaClO for 4 minutes.

3. The method of claim 1, wherein the ultrasonic frequency is 5 KHz to 100 KHz and the ultrasonic treatment time is 0.1 min to 10 min.

4. The method of claim 1 wherein the industrial fermenter has an aeration rate of 2-20 L/min, a tank pressure of 0.03-0.05 mpa, an inoculation amount of 20%-50%, and a culture time of 20-30 d.

5. The method of claim 1 wherein the optimal treatment conditions are 0.7% citric acid, 16 hours, 90° C., and 10 mL of 80% methanol.

* * * * *